(12) United States Patent
Ahrens

(10) Patent No.: US 6,436,144 B1
(45) Date of Patent: Aug. 20, 2002

(54) SHOULDER JOINT ENDOPROSTHESIS

(75) Inventor: Uwe Ahrens, Berlin (DE)

(73) Assignee: aap Implantate AG, Berlin (DE)

( * ) Notice: Subject to any disclaimer, the term of this patent is extended or adjusted under 35 U.S.C. 154(b) by 35 days.

(21) Appl. No.: 09/672,322

(22) Filed: Sep. 28, 2000

(30) Foreign Application Priority Data

Sep. 28, 1999 (DE) ......................... 199 48 141

(51) Int. Cl.$^7$ ................................. A61F 2/40
(52) U.S. Cl. ................................. 623/19.11
(58) Field of Search ................. 623/18.11, 19.11, 623/19.12, 19.13

(56) References Cited

FOREIGN PATENT DOCUMENTS

| DE | 43 14 200 C1 | 7/1994 |
|---|---|---|
| DE | 298 00 975 U1 | 7/1999 |

*Primary Examiner*—David J. Isabella
(74) *Attorney, Agent, or Firm*—Cohen, Pontani, Lieberman & Pavane

(57) ABSTRACT

A shoulder joint endoprosthesis, consisting of a ball joint head and of a stem part which can be anchored in the humerus and has a prosthesis head. The prosthesis head has, on its outer surface, a multiplicity of bores into which pins for locking tubercle fragments can be driven with frictional fit and form fit.

5 Claims, 1 Drawing Sheet

SHOULDER JOINT ENDOPROSTHESIS

BACKGROUND OF THE INVENTION

1. Field of the Invention

The invention relates to a shoulder joint endoprosthesis, consisting of a ball joint head and of a stem part which can be anchored in the humerus and has a prosthesis head.

2. Field of the Invention

A shoulder joint endoprosthesis of this type is known from German reference DE 43 14 200 C1. This concerns the provision of a total endoprosthesis with an artificial rotator cuff.

In the event of a comminuted fracture of the head of the humerus, the detached tendons and tubercles of the rotator cuff must be securely attached to the prosthesis. This attachment must be permanent and be able to take up loads, and it must also be able to restore the natural mobility.

SUMMARY OF THE INVENTION

The invention is therefore based on the object of making available a shoulder joint endoprosthesis with which this type of attachment can be achieved by simple means.

According to the invention, this object is achieved by the fact that the prosthesis head has, on its outer surface, a plurality of bores into which pins for locking tubercle fragments can be driven with frictional fit and form fit.

The openings or bores are arranged in that area of the prosthesis which corresponds to the whole area of the head of the humerus. The large number of such openings or bores provided allows the tubercle fragments to be aligned/positioned very precisely so that the mobility of the arm can be restored in full.

The tubercle fragments are first applied to the appropriate site of the prosthesis head and a pin is then driven through them into the underlying bore. This takes place with a defined impulse. Since the lower or front area of the pin and the bores are of conical design, for example, the pins are held with frictional fit and form fit. The protruding ends of the pins are bent back. By means of this construction according to the invention, it is possible to retain the rotator cuff and restore its natural position.

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention.

DETAILED DESCRIPTION OF THE PREFERRED EMBODIMENTS

Figure 1:
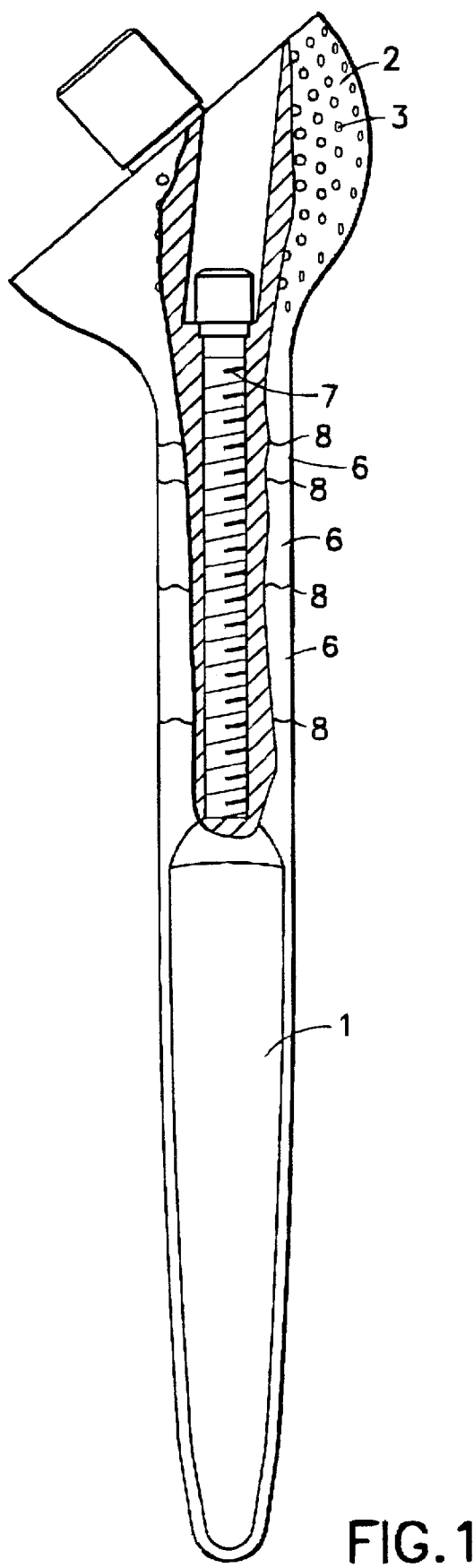
FIG. 1 shows a side view of the stem part, partially in cross section.

The figures do not show the whole endoprosthesis, as this is not necessary for explaining the invention.

The stem part 1 of the prosthesis consists of the prosthesis head 2 and of the stem segments 6 forming the actual stem. The head 2 has a number of bores 3 in its surface. The stem segments 6 are annular. Only the end part has a shape deviating from the circular shape in order to improve anchoring. The mutually facing annular surfaces of the segments 6 have toothed projections 8 which can engage in one another, in other words are complementary.

The prosthesis head 2 and the stem segments 6 are held together, with frictional fit and form fit, by means of a tightening screw 7 which is coaxial to the longitudinal axis of the stem. Anti-rotation is achieved in this way. After the tightening screw has been loosened, the parts 2, 6 can be turned relative to one another in order to obtain optimum alignment of the prosthesis head 2. The number of stem segments 6 used depends on the required length of the stem 1.

Figure 2:
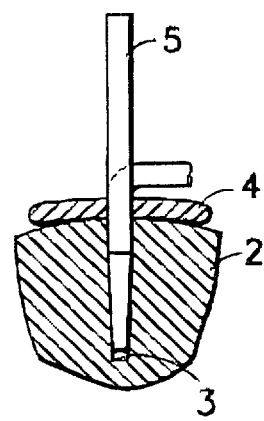
FIG. 2 is an enlarged sectional view of a portion of prosthesis head showing the attachment of the tubercle fragments to the head of the prosthesis.

FIG. 2 shows how the tubercle fragments 4 are fixed by the pins 5 on the outer surface of the prosthesis head, the protruding end being bent back after the pin has been driven in the bore 3. The pins 5 and the bores 3 can have conical or threaded end areas.

Thus, while there have been shown and described and pointed out fundamental novel features of the present invention as applied to a preferred embodiment thereof, it will be understood that various omissions and substitutions and changes in the form and details of the devices illustrated, and in their operation, may be made by those skilled in the art without departing from the spirit of the present invention. For example, it is expressly intended that all combinations of those elements and/or method steps which perform substantially the same function in substantially the same way to achieve the same results are within the scope of the invention. Substitutions of elements from one described embodiment to another are also fully intended and contemplated. It is also to be understood that the drawings are not necessarily drawn to scale but that they are merely conceptual in nature. It is the intention, therefore, to be limited only as indicated by the scope of the claims appended hereto.

What is claimed is:

1. A shoulder joint endoprosthesis, comprising:
   a ball joint prosthesis head;
   a stem part which is anchorable in a humerus and is connected to the prosthesis head, the prosthesis head having an outer surface with plurality of bores; and
   pins driveable into the bores with frictional fit and form fit for locking tubercle fragments.

2. A shoulder joint endoprosthesis as defined in claim 1, wherein each pin and bore have conical engagement surfaces.

3. A shoulder joint endoprosthesis as defined in claim 1, wherein each pin and bore have threaded engagement surfaces.

4. A shoulder joint endoprosthesis as defined in claim 1, wherein the stem is modular consisting of individual annular stem segments, each of the segments having a longitudinal through-bore formed therein, and further comprising a tightening screw, which is coaxial to a longitudinal axis of the stem, arranged so as to pass through the through-bores of the annular segments and the head to connect the prosthesis head to the stem part.

5. A shoulder joint endoprosthesis as defined in claim 4, wherein the annular stem segments have mutually facing annular surfaces that are toothed so that when the tightening screw is loosened, the stem segments can be turned relative to one another, and, when the tightening screw is tightened, there is a frictional fit and form fit between the annular segments.

* * * * *